United States Patent
Sjöberg et al.

(10) Patent No.: US 6,692,750 B1
(45) Date of Patent: Feb. 17, 2004

(54) ALPHAVIRUS EXPRESSION VECTOR

(75) Inventors: Mathilda Sjöberg, Solna (SE); Maarit Suomalainen, Zürich (CH); Henrik Garoff, Stockholm (SE)

(73) Assignee: Bioption AB, Sollentuna (SE)

( * ) Notice: Subject to any disclaimer, the term of this patent is extended or adjusted under 35 U.S.C. 154(b) by 0 days.

(21) Appl. No.: 09/657,312

(22) Filed: Sep. 7, 2000

Related U.S. Application Data

(62) Division of application No. 08/737,608, filed as application No. PCT/SE95/00558 on May 17, 1995, now Pat. No. 6,224,879.

(30) Foreign Application Priority Data

May 18, 1994 (SE) ............................................ 9401709

(51) Int. Cl.⁷ .................. A61K 48/00; A61K 39/12; C12N 5/10; C12N 15/86; C12N 15/63
(52) U.S. Cl. .................. 424/218.1; 435/320.1; 435/69.1; 435/325; 435/366; 435/455; 435/456; 435/5; 435/6; 435/457; 435/69.7; 435/235.1; 424/184.1; 424/185.1; 424/199.1; 424/204.1; 424/93.1; 424/93.2; 424/93.6; 536/23.1; 536/24.1; 536/23.4; 536/23.7; 536/23.71
(58) Field of Search .................. 435/320.1, 69.1, 435/325, 366, 455, 456, 5, 6, 457, 69.7, 235.1; 424/184.1, 185.1, 199.1, 204.1, 218.1, 93.1, 93.2, 93.6; 536/23.1, 24.1, 23.4, 23.7, 23.71

(56) References Cited

U.S. PATENT DOCUMENTS

| | | | |
|---|---|---|---|
| 5,091,309 A | 2/1992 | Schlesinger et al. | |
| 5,217,879 A | 6/1993 | Huang et al. | |
| 5,739,026 A | * 4/1998 | Garoff et al. | 435/240.2 |
| 6,190,666 B1 | * 2/2001 | Garoff et al. | 424/208.1 |

FOREIGN PATENT DOCUMENTS

| | | |
|---|---|---|
| WO | 9210578 | 6/1992 |
| WO | 9527069 | 10/1995 |

OTHER PUBLICATIONS

Linda S. Klavinskis et al, Molecularly Engineered Vaccine Which Expresses an immunodominant T–Cell Epitope Induces Cytotoxic T Lymphocytes That Confer Protection from metal Virus Infection, Journal of Virology, Oct. 1989, p. 4311–4316.*
Barry T. Rouse et al, Antiviral Cytoxic T Lymphocyte Induction and Vaccination, Reviews of Infectious Diseases, vol. 10, No. 1, Jan.–Feb. 1988.*
Rainer Jaenicke, Folding and Association of Proteins, vol. 49, pp. 117–237, 1987.*
Fox, Nature Biotechnology, 2000, vol. 18, pp. 143–144.*
Kmiec, American Scientist, 1999, vol. 87, pp. 240–247.*
Verma et al., Nature, 1997, vol. 389, pp. 239–242.*
Anderson, Nature, 1998, vol. 392, pp. 25–30.*
Liljeström et al., Bio/Technology, vol. 9, pp. 1356–1361 (Dec. 1991).
Liljeström et al., Journal of Virology, vol. 65, No. 8, pp. 4107–4113 (Aug. 1991).
Levis et al., Jouranl of Virology, vol. 64, , No. 4, pp. 1726–1733 (Apr. 1990).
Grakoui et al., Journal of Virology, vol. 63, No. 12, pp. 5216–5227 (Dec. 1989).
Tsiang et al., Journal of Virology, vol. 62, no. 1, pp. 47–53 (Jan. 1988).
Niesters et al., Journal of Virology, vol. 64, No.4, pp. 1639–1647 (Apr. 1990).
Niesters et al., Journal of Virology, vol. 64, No. 9, pp. 4162–4168 (Sep. 1990).
Levis et al., Cell, vol. 44, pp. 137–145 (Jan. 17, 1986).
Kuhn et al., Journal of Virology, vol. 64, No. 4, pp. 1465–1476 (Apr. 1990).
Genbank Accession No. A18788 (WO 92/10578–A).
Frolov et al., Journal of Virology, vol. 68, No. 12, pp. 8111–8117 (1994).
Wang et al., Science, vol. 282, pp. 476–480 (1998).
P. Liljestrom, Current Opinion in Therapeutic Patents, Mar./Apr. 1993, pp. 375–402.
X. Zhou et al., Vaccine, vol. 12, No. 16, pp. 1510–1514 (1994).
C. S. Hahn et al., Proc. Natl. Acad. Sci. USA, vol. 89, pp. 2679–2683 (1992).
Strauss E. G. and J. H. Strauss. 1986. Structure and replication of the alphavirus genome. In The Togaviridae and Flaviviridae. S. S. Schlesinger and M. J. Schlesinger, eds. Plenum Press, New York. pp. 35–90.
Xiong et al., Science, vol. 243, pp. 1188–1191 (1989).
Report and Recommendations of the Panel to Access the NIH Investment in Research on Gene Therapy, Dec. 7, 1995.
Coglan, A., New Scientist, Nov. 25, 2995, p. 14–15.

* cited by examiner

*Primary Examiner*—David Guzo
(74) *Attorney, Agent, or Firm*—Birch, Stewart, Kolasch & Birch, LLP

(57) ABSTRACT

The present invention is directed to alphavirus expression vectors comprising at least part of an alphavirus genome and heterologous RNA inserted downstream of an alphavirus base sequence having translation enhancing activity. Such vectors can be used to achieve enhanced levels of expression of DNA or cDNA coding for a desired product and being complementary to said heterologous RNA after introduction of said vector in eukaryotic cells in cell culture or in a living body. The expression product may have therapeutic or prophylactic activity.

50 Claims, 4 Drawing Sheets

US 6,692,750 B1

ALPHAVIRUS EXPRESSION VECTOR

Figures 1A, 1B:
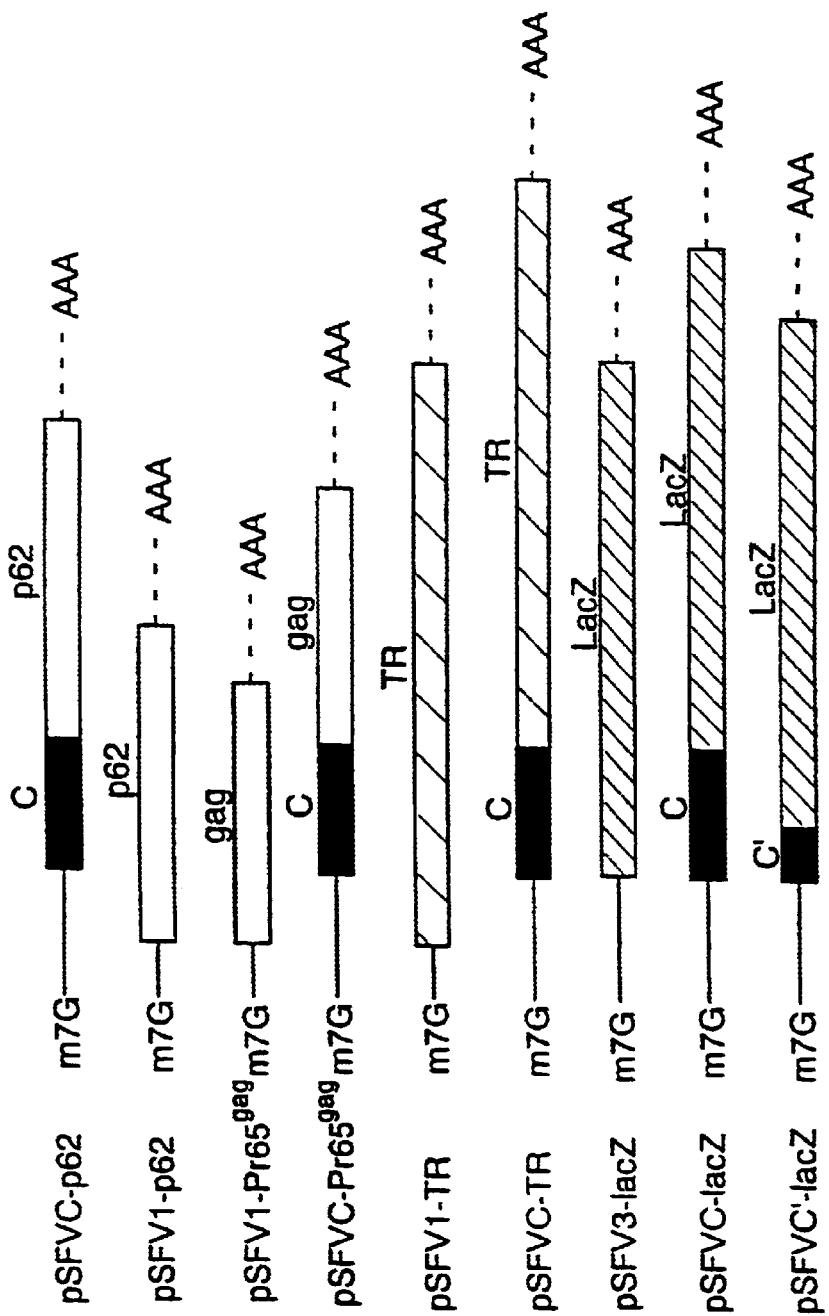

This application is a divisional of application Ser. No. 08/737,608, filed on Nov. 18, 1996 now U.S. Pat. No. 6,224,879. application Ser. No. 08/737,608 is the national phase of PCT International Application No. PCT/SE95/00558 filed on May 17,1995 under 35 U.S.C. §371. The entire contents of each of the above identified applications are hereby incorporated by reference.

BACKGROUND OF THE INVENTION

The present invention is generally related to polynucleotide molecules and to their use for production of desired products after introduction thereof into human or animal cells.

More specifically, the present invention is directed to alphavirus expression vectors comprising at least part of an alphavirus genome and heterologous RNA inserted downstream of an alphavirus base sequence having translation enhancing activity. Such vectors can be used to achieve enhanced levels of expression of DNA or cDNA coding for a desired product and being complementary to said heterologous RNA after introduction of said vector in eukaryotic cells in cell culture or in a living body.

The modern techniques in molecular biology have opened up many completely unforeseen possibilities for the pharmaceutical and biotechnological industry. For instance, it is today possible to clone any gene (once identified) as a DNA (or cDNA) molecule and express it in prokaryotic and/or eukaryotic cells. This has facilitated the production of the corresponding proteins in vitro for therapeutic use and/or prophylactic use, e.g. as a vaccine. Lately the possibilities of gene expression technology have been extended also to in vivo use in whole animals and even in human beings. Illustrative of this recent development are human gene therapy [1] and genetic immunization [2]. In order to express a foreign gene in cells in vivo or in vitro, the gene segment, or the corresponding cDNA, comprising the coding sequences, is usually inserted into a so called expression vector. This vector provides for all elements that are necessary for the transcription and translation of the gene, or the cDNA thereof, within the cell. Today, there exist very efficient expression vectors for bacterial and yeast cells. However, this is not the case for animal, such as mammalian, cells. This creates a large problem when a protein with mammalian specific-modifications has to be produced and isolated for a therapeutic purpose or for prevention of disease or in cases where expression in whole organisms, e.g. the living body of an animal or human, is required. Therefore, in very general terms there is a great demand for new expression vectors for use in animal, e.g. mammalian, cells, which vectors have (i) increased protein expression efficiency, (ii) broadened host cell specificity, and (iii) increased safety.

Recently, a completely new type of DNA expression vectors have been developed for use in animal, e.g. mammalian, cells. These vectors are based on the alphavirus genome.

Alphavirus is a genus belonging to the family Togaviridae having single stranded RNA genomes of positive polarity enclosed in a nucleocapsid surrounded by an envelope containing viral spike proteins.

The Alphavirus genus comprises among others the Sindbis virus, the Semliki Forest virus (SFV), the Ross River virus and Venezuelar, Western and Eastern equine encephalitis viruses, which are all closely related. In particular, the Sindbis and the Semliki Forest viruses have been widely studied and the life cycle, mode of replication, etc, of these viruses are well known and thus, need not to be specifically discussed herein.

Alphaviruses replicate very efficiently in animal cells which makes them valuable as vectors for production of protein and nucleic acids in such cells.

Expression systems based on the Sindbis virus are disclosed in U.S. Pat. No. 5,091,309 and U.S. Pat. No. 5,217,879. The Sindbis virus vectors of U.S. Pat. No. 5,091,309 comprise RNA derived from Sindbis defective interfering (DI) RNA having heterologous RNA inserted therein. In U.S. Pat. No. 5,217,879 self-replicating and self-packaging recombinant Sindbis virus RNA molecules are disclosed comprising a heterologous coding sequence and at least one Sindbis virus junction region able to direct Sindbis virus subgenomic messenger RNA synthesis in a host cell. RNA transcripts are synthesized in vitro by transcription of Sindbis virus cDNA which has been inserted in a plasmid under control of a promoter, such as SP6.

Xiong At al., Science, Vol 243, 1989, 1188–1191[3] also disclose a gene expression system based on Sindbis virus. This system is said to be efficient in a broad range of animal cells. Expression of the bacterial CAT (chloramphenicol acetyltransferase) gene in insect, avian and mammalian cells inclusive of human cells is disclosed therein.

In Bio/Technology, Volume 9, pages 1356–1361, 1991[4], Liljeström and Garoff disclose animal cell expression vectors based on the SFV replicon. When foreign DNA coding sequences are inserted into these vectors, high amounts of foreign protein are obtained.

According to WO 92/10578, an RNA molecule is provided, which is derived from an alphavirus RNA genome and is capable of efficient infection of animal cells, which RNA molecule comprises the complete alphavirus genome regions, which are essential for replication of the said alphavirus RNA, and further comprises an exogenous RNA sequence capable of expressing its function in said host cell, said exogenous RNA sequence being inserted into a region of the RNA molecule which is non-essential to replication thereof. According to WO 92/10578 such RNA molecules can be transferred into animal cells by any means of transfection or by packaging of said RNA molecules into infectious alphavirus particles for later infection of animal cells. In both cases the transfected or infected RNA molecule will be able to replicate within the target animal cell and to express the exogenous RNA sequences inserted into said RNA molecule. Such molecules and strategies for their expression within the cell can be used as vaccines or strategies to vaccinate in order to prevent or treat infection or cancer. In this reference, SFV has been used to illustrate alphaviruses.

The above mentioned expression vectors based on the alphavirus genome have been shown to promote a higher protein expression efficiency than earlier mammalian protein expression systems. They have also been shown to work in almost all higher eukaryotic cell types. Furthermore, they have been complemented with highly stringent safety features to prevent spreading of the virus[5]. Important proteins, to be used for prevention of disease, like the HIV spike protein, have been produced with this system and such proteins have been shown to have a more native-like structure than when produced in other systems[6]. Alphavirus vectors have also been used successfully for genetic immunization[7].

DESCRIPTION OF THE INVENTION

The present invention is directed to a significant and unforeseen improvement of the alphavirus expression vectors.

More specifically, in accordance with the present invention it has been found that there are nucleotide base sequences within the alphavirus genome, which sequences have translation enhancing activity. In comparison to the expression levels of prior known alphavirus vectors, the level of expression of a desired substance which can be obtained according to the present invention is increased about 10-fold.

Thus, the present invention is generally directed to expression of heterologous DNA in eukaryotic cells, alphavirus vectors comprising at least part of an alphavirus genome being used to achieve expression, said vectors further comprising RNA complementary to the heterologous DNA inserted essentially immediately downstream of a nucleotide base sequence having translation enhancing activity.

According to the present invention, such base sequences having translation enhancing activity (also designated translational enhancers) comprise a 5' portion of an alphavirus capsid gene or the complete capsid gene. Suitably, this translational enhancer is endogenous to the alphavirus vector. However, exogenous translational enhancers of another alphavirus species origin might be used, at least occasionally.

Thus, the present invention is also related to a self-replicative and transcription competent recombinant alphavirus RNA molecule comprising at least part of an alphavirus RNA genome and heterologous RNA encoding a substance having biological activity located downstream of an alphavirus base sequence having translation enhancing activity, said translation enhancing base sequence being comprised of a complete alphavirus capsid gene or a 5' portion of said gene.

A suitable embodiment of the present invention is concerned with expression vectors based on the Semliki Forest virus (SFV) genome. The complete SFV capsid gene encodes 267 aminoacid residues, and, thus, comprises 801 bases.

For SFV, a translation enhancing activity has been found to reside in the first 102 bases of this capsid gene, said activity giving rise to a protein production at a level of about 85% of the wild-type capsid protein. This is an about 10-fold increase in comparison to the prior known SFV vectors.

A sequence of said gene comprising the first 81 bases also gives rise to an increased level of expression, although to a less extent.

Thus, the present SFV translational enhancer comprises at least the first 81 bases, and preferably at least the first 102 bases of the capsid gene and at most 801 bases, i.e. a base sequence corresponding to the complete capsid gene.

The sequence of the said 5' portion of the SFV capsid gene comprised of the first 102 bases, reading from 5' to 3' end, is ATGAATTACA TCCCTACGCA AACGTTTTAC GGC-CGCCGGT GGCGCCCGCG CCCGGCGGCC CGTCCT-TGGC CGTTGCAGGC CACTCCGGTG GCTCCCGTCG TC (SEQ ID NO:1).

Modifications of this base sequence (e.g. base deletions, substitutions, and/or additions) having an essentially conserved enhancing activity are also encompassed by the present invention.

In the following illustrative Examples the occurrence of a translational enhancer has been demonstrated for SFV. In view of the homology between various alphavirus species, it can be expected that a similar mechanism of translation enhancement exists in all alphaviruses. However, as the sequence between different alphaviruses vary considerably in the 5' end of the C gene region, it is most likely that some similarities in the features of the secondary and the tertiary structure of the RNA molecule are responsible for the translation enhancing effect. This means that the exact sequences and probably also the length of the translation enhancing regions will vary between different alphaviruses.

The present invention is also related to a DNA molecule comprising DNA sequences complementary to the present recombinant alphavirus RNA molecule, which DNA molecule also may comprise a DNA sequence encoding a promoter, such as SP6, for transcribing the recombinant RNA molecule in cells and additional DNA sequences encoding traits required for plasmid growth in E. coli.

The present alphavirus vectors having enhanced translation capacity can be used for the same purposes as the previously known alphavirus vectors. Thus, they are likely to be very useful for production of substances having biological activities, such as proteins or polypeptides, in eukaryotic cells, especially mammalian ones, which substances can be used for biotechnical or medical purposes. For instance, the heterologous RNA may suitably encode a protein, polypeptide or peptide having therapeutic activity or prophylactic, such as immunogenic or antigenic, activity. Said eukaryotic cells, wherein expression is achieved, can be available as cell cultures or constitute a part of a living organism, such as an animal or human being. The present invention is also concerned with cells transformed with the present recombinant RNA or DNA molecule and cell lines stably transformed with said RNA or DNA molecule.

As stated above, the alphavirus expression vectors are based on the alphavirus genome. This consists of a single-stranded RNA molecule of positive polarity. In the infected cell the 5' ⅔ of this RNA serves as a mRNA for the viral nonstructural polyprotein, which is co- and posttranslationally cleaved into four mature proteins[8, 9]. These proteins form the viral polymerase complex which replicates the genomic RNA via an intermediate of negative polarity[10]. This intermediate also functions as a template for the synthesis of a subgenomic RNA molecule, which is colinear with the 3' ⅓ of the viral genome. This subgenomic transcript (also called 26S mRNA) is translated into the viral structural poly-protein. Processing of this polyprotein is initiated by the amino terminal capsid (C) protein, which autocatalytically cleaves itself from the nascent polyprotein chain[11, 12, 13, 14]. The remaining part of the structural polyprotein is co-translationally. inserted into the membrane of the endoplasmic reticulum and the spike proteins p62 and E1 are released by signal peptidase-mediated cleavage events[15, 16, 17].

The alphavirus expression vectors are suitably constructed from a modified cDNA copy of the viral genome, from which at least part of the structural polyprotein-encoding region has been deleted and replaced with a cloning site[3, 4]. Heterologous cDNA can be inserted into this site and the corresponding recombinant alphavirus genome can be produced by in vitro transcription. When transfected into host cells the recombinant genome is replicated in a wild-type manner since it contains both the non-structural coding region of the alphavirus and the 5' and 3' replication signals. However, instead of the virus structural proteins the subgenomic RNA now directs the synthesis of the heterologous protein. The Semliki Forest virus (SFV) expression system[4] has also been supplemented with an in vivo packaging system whereby recombinant genomes can be packaged into infectious SFV-like particles following co-transfection with a packaging-deficient helper genome, which provides the viral structural proteins[4, 5]. These recombinant particles can be used to infect cells either in vivo or in vitro. The host cell range of the recombinant particles is determined by the alphavirus spike and is therefore very broad. The infected cells will produce recombinant genomes and also high amounts of the heterologous proteins. However, as no virus structural proteins are encoded by the recombinant genomes, no new virus particles will be made, and hence there is no spreading of virus.

Accordingly, one embodiment of the present invention is directed to a method to produce a recombinant alphavirus comprising a recombinant alphavirus RNA genome surrounded by a wild-type alphavirus coat, the said RNA genome comprising the present recombinant RNA molecule, by co-transformation, such cotransfection, of cells with the said recombinant RNA genome and a helper RNA containing expression capacity of alphavirus structural proteins and comprising coding sequences for the alphavirus structural proteins, cis acting replication signals but no encapsidation signals, incubation of the cells and collection of medium containing infectious recombinant alphavirus particles.

The present invention is also related to these co-transformed cells producing the infectious particles and to the infectious particles per se.

As indicated above, a broad range of host cells of animal (including human) origin can be used according to the present invention. Such host cells can be selected from avian, mammalian, amphibian, insect and fish cells. Illustrative of mammalian cells are human, monkey, hamster, mouse and porcine cells. Suitable avian cells are chicken cells.

Furthermore, the present invention can be used both in vitro and in vivo. As per definition, in vitro means a process performed outside a living organism as opposed to in vivo which means that a process is performed inside a living organism.

In accordance with the present invention "transformation" is intended to mean introduction in general of exogenous polynucleotides sequences into the interior of a cell, eukaryotic or prokaryotic, and the exogenous polynucleotide sequence may remain in cell cytoplasm, in nucleus as extrachromosomal (episomal) or may be stably integrated into the cell genome. The mode of transformation is not crucial, but any means, known at present or that may be developed in the future, can be used according to the invention.

A further embodiment of the invention is related to a method for expressing a heterologous RNA sequence encoding a biologically active substance comprising infection of cells in cell culture or in an animal or human individual with the present infectious recombinant alphavirus particles.

Suitably, such expression, when achieved in an animal, will not give rise to any effect beneficial to said animal, but the expression product produced in said animal can be recovered from said animal, e.g. in a body fluid, such as blood, milk or ascites.

The present invention is also related to a pharmaceutical preparations comprising the present recombinant RNA in a physiologically administrable form. Such preparations may comprise the present co-transformed cells producing infectious recombinant alphavirus particles or such infectious particles per se.

In the following experimental part, the Semliki Forest virus (SFV) has been used to illustrate the present invention. The earlier described SFV expression system provides three different plasmid vectors (pSFV1-3) with a cloning site for heterologous DNA in, or immediately after, the 5' untranslated leader sequence of the subgenomic 26S RNA[4]. In Example 2 the expression levels of several different heterologous proteins are compared when using the earlier SFV vectors and when using a new SFV vector in which the complete 26S RNA leader plus the complete C protein gene precedes the heterologous protein gene (=the SFVC-vector). It is evident that heterologous products are produced from SFVC-vectors at a substantially higher level than from the earlier vectors and that all C-fusion proteins have been cleaved into separate authentic products via the autoprotease activity of the C protein (FIG. 2). Quantitation shows that there is about a ten-fold difference in expression level.

In example 3 we have used *E. coli* LacZ (β-galactosidase) gene fusions in order to study where in the C gene the enhancing effect resides. Specifically, various portions of the 5' part of the C gene have been fused to the second codon of the LacZ gene. Expression of these recombinant constructions show that the enhancing effect is located within the 102 first bases of the C gene.

In example 4 we have analyzed whether the effect is expressed on the level of RNA replication and transcription. The production of genomic RNA and subgenomic RNA was compared in high and low producer variants of the LacZ recombinants described in example 3. No differences in RNA levels were found and hence the enhancing effect of the C gene segment must reside on the translational level. This segment most likely contains a specific RNA structure that enhances translational initiation.

DETAILED DESCRIPTION OF DRAWINGS

FIG. 1.

A. Overview of Recombinant Subgenomic RNA Molecules.

Shown are schematic drawings of the subgenomic RNA molecules produced in cells that have been transfected with in vitro transcripts of the indicated plasmids. Note, that only part of the untranslated 5' leader sequence is present in the pSFV1 contructs, whereas the whole leader sequence is present in the pSFV3 constructs[4].

B. Number of C-protein Amino Acid Codons in Plasmids of the pSFVC'-series.

FIG. 2

The Presence of the C Gene Enhances Protein Production.

BHK-21 cells were transfected with RNA transcripts of the following plasmids; pSFV1-p62, pSFVC-p62, PSFV1-TR, pSFVC-TR, pSFV1-Pr65$^{gag}$, pSFVC-Pr65$^{gag}$, pSFV3-LacZ, pSFVC-LacZ, pSFVmSQL and pSFVC-Pr65$^{gag}$ (lanes 1–10, respectively). At 8 h post transfection cells were pulse-labelled with $^{35}$S-methionine for 30 min (lanes 1–6) or 15 min (lanes 7–10) and chased for 15 min (lanes 1–10). Cells were lysed with NP-40 (lanes 1–6) or SDS (lanes 7–10) and aliquots corresponding to $1.6\times10^5$ cells were either extracted with antibodies against SFV E2 (lanes 1–2), the transferrin receptor (lanes 3–4) or against Moloney Murine Leukemia virus (lanes 5–6) or mixed directly with sample buffer (lanes 7–10) and analyzed by SDS-PAGE under reducing conditions followed by fluorography.

FIG. 3

A 102 Base Segment From the C Gene is Responsible for Protein Expression Enhancement.

BHK-21-cells were transfected with RNA transcripts of pSFV3-LacZ, six members of the SFVC'-LacZ series and pSFVC-LacZ as indicated. At 8 h post transfection cells were pulse-labelled with $^{35}$S-methionine for 15 min, chased for 15 min and then lysed with SDS. Aliquots of cell lysates (corresponding to $1.2 \times 10^4$ cells) were mixed with sample buffer and analyzed by SDS-PAGE under reducing conditions. The amount of β-galactosidase or β-galactosidase fusion proteins were quantitated as described in example 2 and corrected for differences in methionine content. Shown is the relative rate of protein synthesis (expressed as percentage of SFVmSQL C-protein synthesis) versus length of the variable C' part of the C'-β-galactosidase fusion proteins.

FIG. 4

Expression Enhancement by the 102 Base Long C Gone Segment is not Mediated Through Increased Replication nor Transcription.

Cells were transfected with RNA transcripts from pSFVmSQL (lane 1), pSFVC'b7-LacZ (lane 2), pSFV3-LacZ (lane 3), pSFV1-Pr55$^{gag}$ (lane 5) or with buffer alone (lane 4). Actinomycin D (1.0 μg/ml) was added 2 h post transfection. At 4 h post transfection $^{14}$C-uridine was added and the cells labelled for 4 h. Total RNA was extracted and aliquots corresponding to $1.4 \times 10^5$ cells were analyzed on an agarose gel under denaturing conditions. Shown is an autoradiogram of the dried gel.

EXAMPLES

Example 1

In this we describe the construction of SFV vectors with heterologous genes that are fused either to the 26S mRNA leader, to the 3' end of the complete C gene or to 5' portions of the C gene. All constructions have been done using the complete SFV cDNA molecule in plasmid pSP6-SFV4[(4)] which have been deposited at the European Collection of Animal Cell Culture, Porton Down, Salisbury, Wiltshire, U.K.; Accession number 91112826. In FIG. 1 we show schematically the coding regions of the various MRNA molecules that are produced from the different vector constructs. The vector constructs are:

(i) pSFVC-p62, which contains the gene for the SFV p62 spike subunit as a wild-type fusion with the C gene. It was constructed by ligating the large SpeI/NsiI-fragment (12 kbp) from pSP6-SFV4 to the small NsiI/SpeI-fragment (2.6 kbp) of a pSP6-SFV4 where two termination codons had been introduced at position 9866–9871 in pSP6-SFV4, in the region encoding the N-terminal part of E1 by site directed mutagenesis.

(ii) pSFV1-p62, which contains the gene for the SFV p62 spike subunit fused to the 5' SFV subgenome region at position 31 in the 26S MRNA leader sequence (SFV-1 vector variant)[(4)]. This was constructed by ligating the large SpeI/NsiI-fragment (11 kbp) from pSP6-SFV4/ΔC to the small NsiI/SpeI-fragment (2.6 kbp) in (i). The pSP6-SFV4/ΔC was constructed from pSP6-SFV4 by a deletion of the C gene[(18)].

(iii) pSFV1-TR, which contains the human transferrin receptor gene in a fusion with the 5' SFV subgenome region at position 31 in the 26S RNA leader sequence [(4)].

(iv) pSFVC-TR, which contains the human transferrin receptor gene in a fusion with the 5' SFV subgenome encompassing the complete 26S RNA leader sequence plus the whole C gene. The precise fusion of C and TR genes was carried out by PCR .sup. (19, 20). The terminal primers used for the amplification of the fused DNA were: 5° CAACGGAAAAACGCAGCAGC 3' (the 5' end primer; SEQ ID NO:2) and 5' CTTTGCTGAGTTTAAATTCACG 3' (the 3' end primer; SEQ ID NO:3). The fusion primers used were:5' GATCTAGCT- TGATCCATCATCCACTCTTCGGACCCCTCGGG 3' (C gene fragment primer; SEQ ID NO:4) and 5' CCCGAGGGGTCCGAAGAGTGGATGATG-GATCAAGCTAGATCAGC 3' (TR gene fragment primer; SEQ ID NO:5). pSFVC-TR was constructed by ligating the 896-bp Csp45I-NdeI fusion fragment to the 10679-bp SpeI-Csp45I fragment of pSFV-C .sup.(18) and the 2744-bp NdeI-SpeI fragment of pSFV1-TR .sup.(4). The 896-bp Csp45I-NdeI fragment of pSFVC-TR originating from the PCR reaction was checked by sequencing.

(v) pSFV1-Pr65gag, which contains the gene for the Moloney Murine Leukemia virus (M-MuLV) gag precursor in fusion with the 5' SFV subgenome region at position 31 in the 26S mRNA leader sequence. This was constructed by insertion of a 1770-bp PstI-DraIII-fragment from PNCA (Colicelli, 1988) containing the Pr65gag gene, into pSFV1 via subcloning steps in pGEM-1 and pGEM-7Zf (+) (Promega). The subcloning steps introduced a 5' BamH1 and a 3' SmaI site flanking the Pr65gag gene. The 5' noncoding M-MuLV sequence was deleted by replacing the 5' 177-bp BamH1-PstI fragment with a synthetic 135-bp BamH1-PstI fragment, which was made from the following two overlapping oligonucleotides; 5' ATTCTGATTG-GATCCAGCACCATGGGCCAGACTGTTAC-CACTCCCTTA AGTTTGACCTTAGGTCACTG-GAAAGATGTCGAGCGGATCGCTCACAACCAG 3' (SEQ ID NO:6) and 5' GGTTGGCCATTCTGCA-GAGCAGAAGGTAACCCAACGTCTCTTCT-TGACATCT ACCGACTGGTTGTGAGCGATC-CGCTCGACATCTTTCCAGTGACCTAA 3' (SEQ ID NO:7). GGTTGGCCATTCTGCAGAGCAGAAGG-TAACCCAACGTCTCTTCTTGAC ATCTAC-CGACTGGTTGTGAGCGATCCGCTCGA-CATCTTTCCAGTGACC TAA 3'.

(vi) pSFVC-Pr65$^{gag}$, which contains the M-MuLV gag precursor gene in a fusion with the SFV 5' subgenome region encompassing the complete 26S RNA leader plus the C gene. This plasmid was constructed by a PCR fusion of the SVF C gene to the second codon of the Pr65$^{gag}$ gene. The fusion primers used were: 5' GGGAGTGGTAACAGTCTGGCCCACTCT-TCGGACCCCTCGG 3' (C gene fragment primer; SEQ ID NO:8) and 5' CCCGAGGGGTCCGAA-GAGTGGGGCCAGACTGTTACCACTCCC 3' (Pr65$^{gag}$ gene fragment primer; SEQ ID NO:9). The terminal primers for amplification of the fused DNA were: 5' CAACGGAAAAACGCAGCAGC 3' (the 5' end primer; SEQ ID NO:2) and 5' CAAGGCTTC-CCAGGTCACG 3' (the 3' end primer; SEQ ID NO:10). The pSFVC-pr65$^{gag}$ was then constructed by ligation of the 562-bp Csp45I-PstI C-Pr65$^{gag}$ fusion fragment to the 10679-bp SpeI-Csp45I from pSFV-C .sup.(18) and the 2492-bp PstI-SpeI fragment of pSFV1-Pr65$^{gag}$. The 562-bp Csp45I-PstI fragment of pSFVC-Pr65$^{gag}$ originating from the PCR reaction was checked by sequencing.

(vii) pSFVC-LacZ, which contains the LacZ (β-galactosidase) gene encoding amino acid residues 2–1025 in a fusion with the 5' SFV subgenome region at position 53 in the 26S RNA after the complete untranslated leader sequence (SFV3 vector, [(4)])

(viii) pSFVC-LacZ, which contains the LacZ gene as above in a fusion with the SFV 5' subgenome region encompassing the complete 26S mRNA leader sequence plus the complete C gene. This was constructed by insertion of the small LacZ-containing BamH1-fragment, (3 kbp) from pSFV3-LacZ in the PSFVC$^{BamH1}$. The PSFVC$_{BamH1}$ contains only the C protein gene of the structural SFV genome, directly followed by a BamH1 site. This plasmid was constructed by ligation of the large SpeI-Csp45I fragment (10679-bp) from pSP6-SFV4 to a PCR-generated 440-bp Csp45I-BamH1 3' end fragment of the C gene and the 874-bp BamH1-Spe1 fragment of pSFV1 (ref. Liljestrom & Garoff, Biotechnology 1991). Primers used in the PCR reaction were: (1)5' CAACG-GAAAAACGCAGCAGC 3' (the 5' end primer; SEQ ID NO:2) and (2) 5' CTCAAGGAGTCATGGATC-CCACTCTTCGGACCCCTCGGG 3' (the 3' end primer; SEQ ID NO:11).

(ix) pSFVC'-LacZ, which contains the LacZ gene in a fusion with the 5' subgenome region encompassing the complete 25S mRNA leader plus a 5' portion of the C gene. This was constructed as follows: serial deletions in the C-protein gene of pSP5-SFV4 was made by limited digestion with nuclease Bal 31, starting from the Csp45I site at position 7781. The ends were blunted with Klenow fragment and T4 DNA polymerase and ligated to a mixture of BamH1-linkers (8-, 10- and 12-mers; Promega, Madison, Wis., USA). The 5 large SpeI-BamH1 fragments (approximately 10.3 kbp) from the deletion series were ligated to the small, LacZ gene containing BamH1-SpeI fragment from pSFV3-LacZ.

(x) pSFVmSQL, which is a control plasmid and contains the complete SFV genome. It harbours mutations in the structural gene region which specifies the maturation cleavage site of p62. Because of these mutations the p62 subunit is not cleaved to E2 and E3[21, 5].

Figure 2:
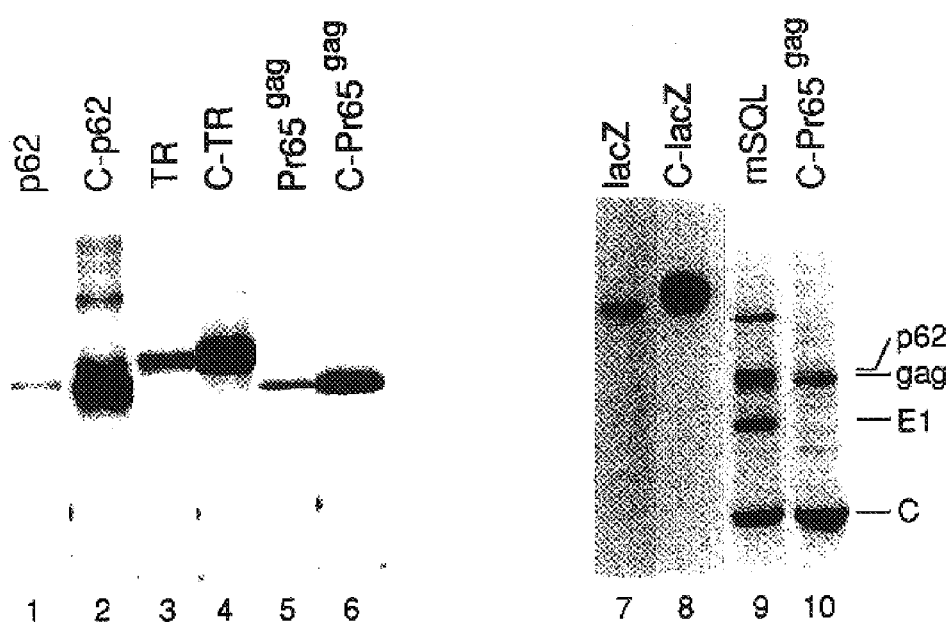

The detailed protocols for all molecular biological techniques used are described in Molecular Cloning[22], Example 2
The Presence of the C Gene Enhances Protein Production RNA was synthesized in vitro using plasmids pSFV1-p62, pSFVC-p62, pSFV1-TR, pSFVC-TR, pSFV1-Pr65$^{gag}$, pSFVC-Pr65$^{gag}$, pSFV1-LacZ, pSFVC-LacZ and pSFVm-SQL as templates. These were transfected into BHK-21 cells and at 8 h post transfection the cells were metabolically labelled with $^{35}$S-methionine for 15 or 30 min as indicated in the legend of FIG. 2. FIG. 2 shows the relative level of synthesis of the homologous p62-protein (lanes 1 and 2), the transferrin receptor (lanes 3 and 4), the M-MuLV gag-precursor protein (lanes 5, 6, and 10), the β-galactosidase-protein (lanes 7 and 8) when expressed alone (lanes 1, 3, 5 and 7) or in tandem with the C-protein (lanes 2, 4, 6, 8 and 10). The synthesis of the structural SFV proteins (C, p62 and E1) are shown in lane 10. Immunoprecipitations from cell lysates (lanes 1–6) or aliquots of total cell lysates (lanes 7–10) are shown.

When expressed from pSFV1-based recombinant genomes SFV p62, TR and M-MuLV gag (lane 1, 3 and 5, respectively) were all synthesized at a comparable low level. However, when these proteins were expressed as C fusion proteins, a dramatic increase in their expression levels where obtained (lanes 2, 4 and 6). Quantitations showed that the increase was approximately 10-fold for all three proteins. The autolytic cleavage that releases the C-protein from the virus structural polyprotein was apparently effective also in the artificial C-Pr65$^{gag}$ and C-TR polyproteins; there was no sign of slow migrating polypeptides which could represent uncleaved fusion proteins (lanes 4 and 6).

In the pSFV1-based genomes only the 5' part of the 26S leader sequence is present, while the subgenome derived from pSFVC contain the whole 5'-gleader. Therefore, the results indicate that the 3' part of the leader sequence or the presence of the C-sequence influence the expression level. In order to find out which region was responsible for enhancing expression we compared the level of β-galactosidase production in cells transfected with either the SFV3-LacZ genome (which contains the whole leader sequence (FIG. 2, lane 7) or the SFVC-LacZ genome (which contains the whole leader sequence plus the C gene sequence) (FIG. 2, lane 8). The latter genome directed the synthesis of an uncleaved C-β-galactosidase fusion protein (1.263 amino acids long, approximately 145 kDa). Quantitation showed that the expression of the C-β-galactosidase fusion protein was approximately 8 times higher than the expression of β-galactosidase from the SFV3-LacZ genome. This increase was as large as that observed above for SFV1 in comparison to SFVC. From these observations we conclude that the presence of C gene sequence in the expression vector has a strong positive effect on SFV-driven production. The most likely reason for the inhibition of cleavage in the C-β-galactosidase construct is a proline residue at position+2, counted from the site cleaved by the capsid protease.

To correlate the level of protein production from an SFVC-genome to that from the wild-type-like SFV genome, we compared the amount of C-protein produced in cells transfected with in vitro transcripts of pSFVmSQL (FIG. 2, lane 9) to the amounts of C and gag-precursor in cells transfected with the SFVC-Pr65$^{gag}$ RNA (FIG. 2, lane 10). The amount of C-protein at 8 h post transfection was indistinguishable in the two transfections. Furthermore, Pr$_{65}$$^{gag}$ and SFV spike proteins were produced at comparable levels, thus showing that the introduction of the C-gene into the expression vector increased the production of heterologous proteins to a level normally obtained for the structural proteins in a wild-type SFV infection.

In this example RNA transcription and transfection was done as follows: RNA transcripts of SpeI-linearized plasmids were synthesized in vitro as described previously[4] and transfected into BHK21 cells (American Type Culture Collection) by electroporation. In brief, 8×10$^6$ cells (suspended in 0.8 ml of Ca$^{2+}$/Mg$^{2+}$-free PBS) were mixed with in vitro made RNA (20 μl of the transcription mix) in a 0.4-cm electroporation cuvette (Bio-Rad Laboratories AB, Solna, Sweden) and exposed to two consecutive pulses at 0.85 kV and 25 μF (BioRad Gene Pulser, without the pulse controller unit). The cells were suspended in 15 ml complete SHK-medium, consisting of BHK-21 medium (Gibco) supplemented with 10% (v/v) tryptose phosphate broth (Gibco, Madison, Wis., USA), 5% (v/v) fetal calf serum, 20 mM N-2-hydroxyethylpiperazine-N'-2-ethanesulphonic acid (HEPES) pH 7.3, plated on 3.3 cm tissue culture dishes (3 ml/dish) and incubated at 37° C.

Metabolic labelling with $^{35}$S-methionine was done as follows: At 8 h post transfection the cells were rinsed twice with PBS, 1.0 ml Eagles minimal essential medium lacking methionine and supplemented with 20 mM HEPES was added and the cells incubated for 30 min at 37° C. The medium was removed and 3.7 MBq (100 μCi) $^{35}$S-methionine in 1.0 ml of the same medium was added and the cells incubated for 15 or 30 min (pulse). The labelling medium was removed and 1.0 ml of EMEM supplemented with 20 mM HEPES was added and the cells further incubated for 15 or 30 min (chase). At the end of the chase the cells were rinsed twice with PBS and solubilized in 0.30 ml of 10 mg/ml SDS or 10 mg/ml Nonidet P40 (NP-40) lysis buffer containing 50 mM Tris-HCl, 0.15 M NaCl and 2.0 mM EDTA, final pH 7.6. Phenylmethylsulfonyl fluoride (PMSF; 0.2 mM), N-ethylmaleimide (0.1 mM) and pepstatin A (1 µg/ml) was added to the lysis buffer before use. Cells disrupted with SDS lysis buffer were sonicated for 20 min at room temperature. Cell nuclei from NP-40 lysed cells were pelleted by centrifugation (5 min at 14.000×g).

Immunoprecipitations were done as follows: Transferrin receptor was precipitated with the OKT9 monoclonal anti-TR antibody (a gift from T. Ebel) the M-MuLV gag precursor with a polyclonal anti-MuLV serum (HC 185; Quality Biotechnology Incorporated) and the p62 with a monoclonal anti E2-antibody (UM 5.1; Boere et al. 1984). Aliquots of SDS-lysates of $^{35}$S-methionine labelled cells (100 µl) were diluted 10 times with 10 mg/ml NP-40 lysis buffer, and an excess of the appropriate antibody was added together with 40 µl protein A-Sepharose slurry (Pharmacia, Uppsala, Sweden; 50% w/v in 10 mM Tris-HCL, pH 7.5) and the samples were rotated end over end for 16 h at+40° C. When linking antibodies were necessary, rabbit anti-mouse immunoglobulin (Dacopatts, Glostrup, Denmark) were also added. The immune complexes were washed as described (Wahlberg and Garoff 1989) and prepared for SDS-PAGE.

SDS-PAGE was done as follows: Washed immune complexes or samples of cell lysates were mixed with SDS-PAGE sample buffer (giving the final concentrations; 0.15 M Tris-HCL, pH 8.8, 0.19 g/ml glycerol, 31 mg/ml SDS, 3.8 mM EDTA, 0.77 mM methionine, 0.15 mg/ml bromphenol blue and 38.5 mM dithiothreitol) heated for 3 min at 95° C., cooled and alcylated with iodoacetamide (final concentration 0.10 M). Finally, the proteins were separated on 11% acrylamide gels as described (Maizel 1971). After electrophoresis the gels were immersed in 10% (v/v) trichloroacetic acid and 40% (v/v) methanol, incubated for 30 min and dried. Gels containing radio-labelled material were exposed to Kodac XAR films for autoradiography.

Quantitations were done as follows: Dried acrylamide-gels that contained radio-labelled material were exposed to a Bas-III Image Plate (Fuji Photo Film Corp.). The image plate signals were digitized and the amount of radioactivity in different parts of the dried gels were analyzed using the Fuji Bio-Image analyze system Bas 2000 (Fuji Photo film Corp.).

Example 3
A 102 Base Segment From the 5' Portion of the C Gene is Mediating the Expression Enhacement.

Figure 3:
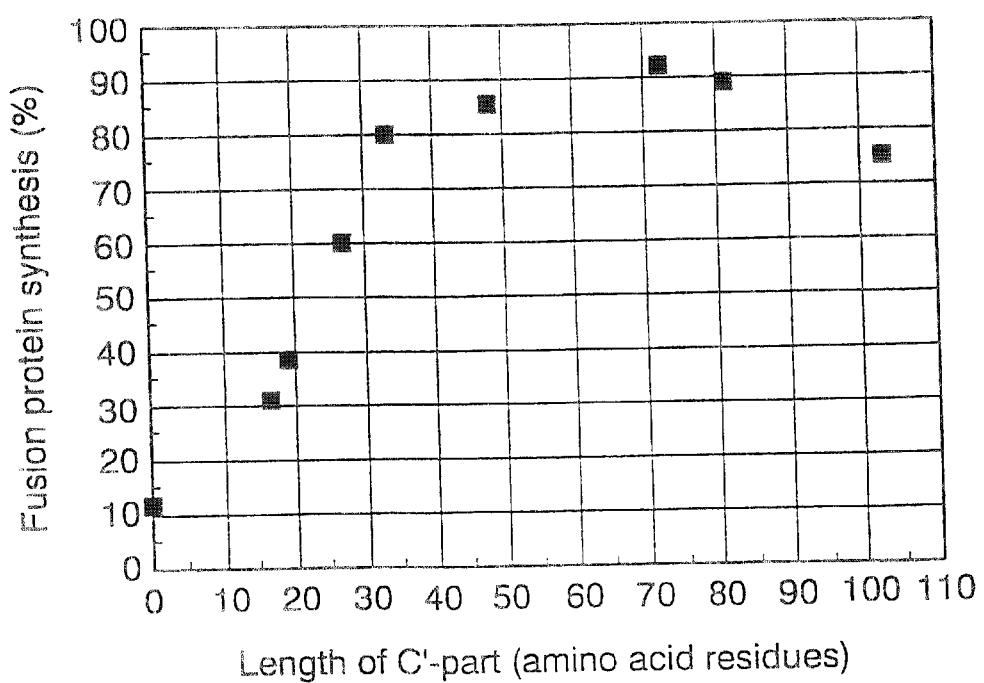

As a first step in elucidating the mechanism of expression enhancement we addressed the question whether the full C-gene sequence, or only a portion of it, was sufficient to promote high levels of protein production. To this end various plasmids (C'-LacZ chimeras), which contained increasing portions of the 5' part of the C-gene (C') fused to the β-galactosidase-gene were constructed (FIG. 1). These plasmids were used as templates for RNA transcription in vitro, the RNAs were transfected into BHK-21 cells and the cells were pulse-labelled for 15 min and chased for 15 min as described in example 2. Transfection efficiencies were higher than 95% in all cases, as judged by β-galactosidase staining in situ. At the end of the chase period cells were lysed in SDS and aliquots of the cell lysates were analyzed by SDS-PAGE under reducing conditions. The amount of radioactivity associated with the fusion proteins was quantitated as described in example 2. FIG. 3 shows the fusion protein production (expressed as percentage of SFVmSQL C-protein production) as a function of the number of C-protein derived amino acids in the fusion protein. The protein production from the longer constructs (containing more than 34 C-protein derived amino acid residues) reached a level of 85% of the wild-type C-protein produc-tion. This is as high as that obtained from the SFVC-LacZ construct described in example 2. The shorter ones (containing 16, 19 and 27 C-protein derived amino acid residues, respectively) were produced at a considerably lower level. Thus, the results demonstrate that a 102 bases long portion of the 5' C-gene (b1) was mediating the increased expression.

In this example RNA transcription, transfection, labelling and SDS-PAGE were done as described in example 2. β-galactosidase staining of methanol fixed BHK-21 cells in tissue culture dishes was done as described by Sanes[23].

Example 4
Expression Enhancement by the 102 Basis Long C-gene Segment is Mediated Through Increased Translation.

Figure 4:
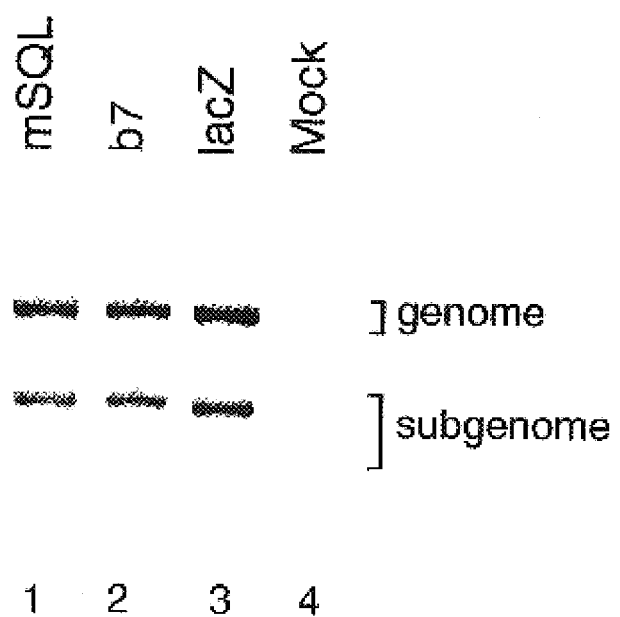

The fact that only a short stretch of the C-gene sequences was needed for optimal protein production makes it unlikely that the effect is mediated in trans (i.e. by the capsid polypeptide chain). A cis acting (i.e. RNA mediated) mechanism, which influences the efficiencies of either transcription or translation, would seem to be a more likely explanation. In order to determine whether the C-gene segment affected the levels of genomic and subgenomic RNAs, the intracellular amounts of these two RNA species were measured in cells transfected with either "high" or "low" producer genomes. Transfected cells were cultured in the presence of Actinomycin D in order to suppress any residual host cell RNA synthesis. At 4 h post transfection $^{14}$C-uridine was added and cells were incubated for 4 h. Total RNA was prepared from the labelled cells and subjected to electrophoresis through 1.0% agarose gels under denaturing conditions. Gels were dried and the amount of radioactivity in different bands were quantitated as described in example 2. FIG. 4 shows an autoradiography of a dried gel: lane 1, SFV-mSQL; lane 2, the high producing SFVC'b7-LacZ; lane 3, the low producing pSFV3-LacZ; lane 4, mock transfection without RNA and lane 5, SFV1-Pr55$^{gag}$; which contains the coding sequence of the Gag-precursor of Human immunodeficiency virus type I. The subgenomic RNA of the SFV1-Pr55$^{gag}$ genome is about 1500 bases shorter than that of SFV-mSQL and the SFVC-LacZ genomes, thus, facilitating the identification of these transcripts. Subgenomic RNAs were found to be synthesized at comparable levels in all transfections. Quantitations indicated that the levels of synthesis varied at the most by a factor of two and did not correlate with the level of protein production. Nor were there any significant differences detected in the levels of the genomic RNA. Thus, neither the replication nor the transcription of the various genomes were effected. Therefore, it is concluded that the increased protein production is a consequence of increased translational efficiency.

In this example $^{14}$C-uridine labelling was done as follows: Transfected cells were directly plated and incubated for 2 h at 37° C. Then 1.0 µg/ml of Actinomycin D was added to the medium and the incubation continued for 2 h. At 4 h post transfection the medium was removed, 75 kBq of $^{14}$C-uridine (2.1 GBq/mmol; NEC-167, Dupont) was added in 1.5 ml complete BHK medium and the cells were incubated for 4 h at 37°. The labelling medium was removed and the cells lysed by addition of 1.0 ml of a phenol based nucleic acid extraction cocktail (Trizol™; Gibco).

RNA purification and denaturating agarose gel electrophoresis was done as follows: Total RNA from $^{14}$C-uridine labelled cells was purified by Trizol™ system as described by the manufacturer (Gibco) and dissolved in 20 µl RNase free H$_2$O. Aliquots were prepared for formaldehyde agarose gel electrophoresis and the RNA was separated in a 1.0%

Seaplaque agarose (FMC Bioproducts, USA) gel as described (Sambrook 1989). After electrophoresis the gel was immersed in 10% trichloroacetic acid, incubated at a room temperature for 30 min and dried. The radio-labelled RNA bands were visualized by autoradiography and quantitated as described in example 2.

References

1. Special Issue. Gene Therapy. 1993. Therapeutic strategies and commercial prospects. Trends in Biotechnology 11:155–215.
2. Nabel, G. J., and Felgner, P. L. 1993, Direct gene transfer for immunotherapy and immunization. Bio/Technology 11:211–215.
3. Xiong, C., Levis, R., Shen, P., Schlesinger, S., Rice, C. M., and Huang, H. V. 1989. Sindbis virus: An efficient, broad host range vector for gene expression in animal cells. Science 243:1188–1191.
4. Liljeström, P., and Garoff, H. 1991. A new generation of animal cell expression vectors based on the Semliki Forest virus replicon. BioTechnology 9:1356–1361.
5. Berglund, P., Sjöberg, M., Garoff, H., Atkins, G. J., Brian, J., Sheahan, B. J., and Liljeström, P. 1993. Semliki Forest virus expression system: Production of conditionally infectious recombinant particles. Bio/Technology 11:916–920.
6. Paul, N., Marsh, M., McKeating, J. A., Schulz, T. F., Liljeström, P., Garoff, H., and Weiss, R. A. 1993. Expression of HIV-1 envelope glyco-protein by Semliki Forest virus. Aids Research and Human Retroviruses 9:963–970.
7. London, S. D., Schmaljohn, A. L., Dalrymple, J. M., and Rice, C. M. 1992. Infectious enveloped RNA virus antigenic chimeras. Proc. Natl. Acad. Sci. USA 89:207–211.
8. Ding, M., and Schlesinger, M. J. 1989. Evidence that Sindbis virus nsP2 is an autoprotease which processes the virus nonstructural polyprotein. Virology 171:280–284.
9. Hardy, W. R., and Strauss, J. H. 1989. processing the nonstructural polyproteins of Sindbis virus: nonstructural proteinase is in the C-terminal half of nsP2 and functions both in cis and in trans. J. Virol. 63:4653–4664.
10. Strauss, E. G., and Strauss, J. H. 1986. Structure and replication of the alphavirus genome, 35–90. In S. S. Schlesinger and M. J. Schlesinger (ed.), The Togaviridae and Flaviviridae, Plenum Press, New York.
11. Aliperti, G., and Schlesinger, M. J. 1978. Evidence for an autoprotease activity of Sindbis virus capsid protein. Virology 90:366–369.
12. Choi, H.-K., Tong, L., Minor, W., Dumas, P., Boege, U., Rossmann, M. G., and Wengler, G. 1991. The crystal structure of Sindbis virus core protein and a proposed structure of the capsid. Nature 354:37–43.
13. Hahn, C. S., and Strauss, J. H. 1990. Site-directed mutagenesis of the proposed catalytic amino acids of the Sindbis virus capsid protein autoprotease. J. Virol. 64:3069–3073.
14. Melancon, P., and Garoff, H. 1987. Processing of the Semliki Forest virus structural polyprotein: role of the capsid protease. J. Virol. 61:1301–1309.
15. Garoff, H., Huylebroeck, D., Robinson, A., Tillman, U., and Liljeström, P. 1990. The signal sequence of the p62 protein of Semliki Forest virus is involved in initiation but not in completing chain translocation. J. Cell Biol. 111:867–876.
16. Hashimoto, K., Erdei, S., Keränen, S., Saraste, J., and K ääriäinen, L. 1981. Evidence for a separate signal sequence for the carboxy-terminal envelope glycoprotein E1 of Semliki Forest virus. J. Virol. 38:34–40.
17. Liljeström, P., and Garoff, H. 1991. Internally located cleavable signal sequences direct the formation of Semliki Forest virus membrane proteins from a polyprotein precursor. J. Virol. 65:147–154.
18. Suomalainen, M., Liljeström, P., and Garoff, H. 1992. Spike protein-nucleocapsid interactions drive the budding of alphaviruses. J. Virol. 66:4737–4747.
19. Horton, R., Hunt, H., Ho, S., Pullen, J., and Pease, L. 1989. Engineering hybrid genes without the use of restriction enzymes: gene splicing by overlap extension. Gene 77:61–68.
20. Yon, J., and Friend, M. 1989. Precise gene fusion by PCR. Nucleic Acid Res. 17:4895.
21. Salminen, A., Wahlberg, J. M., Lobigs, M., Liljeström, P., and Garoff, H. 1992. Membrane fusion process of Semliki Forest virus II: Cleavage dependent reorganization of the spike protein complex controls virus entry. J. Cell Biol. 116:349–357.
22. Sambrook, J., Fritsch, E. F., and Maniatis, T. 1989. Molecular Cloning. A Laboratory Manual, p. Cold Spring Harbor Laboratory Press, Cold Spring Harbor.
23. Sanes, J., Rubenstein, J. L. R., and Nicolas, J.-F. 1986. Use of recombinant retrovirus to study post-implantation cell lineage in mouse embryos. EMBO J. 5:3133–3142.

SEQUENCE LISTING

<160> NUMBER OF SEQ ID NOS: 11

<210> SEQ ID NO 1
<211> LENGTH: 102
<212> TYPE: DNA
<213> ORGANISM: Artificial Sequence
<220> FEATURE:
<223> OTHER INFORMATION: 5' portion of SFV capsid gene

<400> SEQUENCE: 1

```
atgaattaca tccctacgca aacgttttac ggccgccggt ggcgcccgcg cccggcggcc      60
cgtccttggc cgttgcaggc cactccggtg gctcccgtcg tc                        102
```

<210> SEQ ID NO 2
<211> LENGTH: 20
<212> TYPE: DNA
<213> ORGANISM: Artificial Sequence
<220> FEATURE:
<223> OTHER INFORMATION: 5' terminal primer used for the amplification
      of fused DNA of capsid and human transferrin genes

<400> SEQUENCE: 2
caacggaaaa acgcagcagc                                                    20

<210> SEQ ID NO 3
<211> LENGTH: 22
<212> TYPE: DNA
<213> ORGANISM: Artificial Sequence
<220> FEATURE:
<223> OTHER INFORMATION: 3' terminal primer used for the amplification
      of fused DNA of capsid and human transferrin genes

<400> SEQUENCE: 3
ctttgctgag tttaaattca cg                                                 22

<210> SEQ ID NO 4
<211> LENGTH: 41
<212> TYPE: DNA
<213> ORGANISM: Artificial Sequence
<220> FEATURE:
<223> OTHER INFORMATION: C gene fragment primer for fusion of capsid and
      human transferrin genes

<400> SEQUENCE: 4
gatctagctt gatccatcat ccactcttcg gacccctcgg g                            41

<210> SEQ ID NO 5
<211> LENGTH: 44
<212> TYPE: DNA
<213> ORGANISM: Artificial Sequence
<220> FEATURE:
<223> OTHER INFORMATION: TR gene fragment primer for fusion of capsid
      and human transferrin genes

<400> SEQUENCE: 5
cccgaggggt ccgaagagtg gatgatggat caagctagat cagc                         44

<210> SEQ ID NO 6
<211> LENGTH: 99
<212> TYPE: DNA
<213> ORGANISM: Artificial Sequence
<220> FEATURE:
<223> OTHER INFORMATION: oligonucleotide overlapping with SEQ ID NO:7 to
      make a synthetic 135-bp BamH1-PstI fragment

<400> SEQUENCE: 6
attctgattg gatccagcac catgggccag actgttacca ctcccttaag tttgacctta        60
ggtcactgga aagatgtcga gcggatcgct cacaaccag                               99

<210> SEQ ID NO 7
<211> LENGTH: 99
<212> TYPE: DNA
<213> ORGANISM: Artificial Sequence
<220> FEATURE:
<223> OTHER INFORMATION: oligonucleotide overlapping with SEQ ID NO:6 to
      make a synthetic 135-bp BamH1-PstI fragment

<400> SEQUENCE: 7
ggttggccat tctgcagagc agaaggtaac ccaacgtctc ttcttgacat ctaccgactg        60

```
gttgtgagcg atccgctcga catctttcca gtgacctaa                          99

<210> SEQ ID NO 8
<211> LENGTH: 42
<212> TYPE: DNA
<213> ORGANISM: Artificial Sequence
<220> FEATURE:
<223> OTHER INFORMATION: C gene fragment primer for fusion of capsid
      gene to Pr65gag

<400> SEQUENCE: 8
gggagtggta acagtctggc cccactcttc ggacccctcg gg                      42

<210> SEQ ID NO 9
<211> LENGTH: 42
<212> TYPE: DNA
<213> ORGANISM: Artificial Sequence
<220> FEATURE:
<223> OTHER INFORMATION: Pr65gag gene fragment primer for fusion of
      capsid gene to Pr65gag

<400> SEQUENCE: 9
cccgaggggt ccgaagagtg gggccagact gttaccactc cc                      42

<210> SEQ ID NO 10
<211> LENGTH: 19
<212> TYPE: DNA
<213> ORGANISM: Artificial Sequence
<220> FEATURE:
<223> OTHER INFORMATION: 3' terminal primer used for the amplification
      of fused DNA capsid Pr65gag

<400> SEQUENCE: 10
caaggcttcc caggtcacg                                                19

<210> SEQ ID NO 11
<211> LENGTH: 33
<212> TYPE: DNA
<213> ORGANISM: Artificial Sequence
<220> FEATURE:
<223> OTHER INFORMATION: 3' primer used in the construction of pSFVC
      BamH1

<400> SEQUENCE: 11
gagtcatgga tcccactctt cggaccccte ggg                                33
```

What is claimed is:

1. A method for producing a recombinant alphavirus comprising a recombinant alphavirus RNA genome surrounded by a wild-type alphavirus coat;

the RNA genome comprising a self-replicative and transcription competent recombinant alphavirus RNA molecule comprising at least part of an alphavirus RNA genome and heterologous RNA encoding a substance having biological activity located downstream of and operatively linked to an alphavirus base sequence having translation enhancing activity, the translation enhancing base sequence being comprised of a complete alphavirus capsid gene or a portion thereof;

comprising:

i) introducing the recombinant alphavirus RNA genome and a helper RNA encoding alphavirus structural proteins and comprising coding sequences for the alphavirus structural proteins, cis acting replication signals but no encapsidation signals into cells;

ii) producing infectious recombinant alphavirus particles by incubating the cells in a medium; and iii) collecting the medium containing infectious recombinant alphavirus particles.

2. The method of claim 1, in which, after introduction of said recombinant RNA genome into the cells, the heterologous gene product is expressed in the cells as a fusion product with the complete capsid protein or with an amino terminal portion of the capsid protein encoded by a portion of the capsid gene.

3. The method of claim 1, wherein the alphavirus is Semliki Forest virus.

4. The method of claim 1, wherein the translation enhancing base sequence comprises residues 1 to 102 of SEQ ID NO:1.

5. The method of claim 1, wherein the translation enhancing base sequence comprises residues 1 to 81 of SEQ ID NO:1.

6. The method of claim 1, wherein the heterologous RNA is expressed as a fusion product that is cleaved at its fusion site by the autolytic protease activity of the capsid protein.

7. The method of claim 1, wherein the heterologous RNA sequence encodes a protein or a polypeptide comprising an antigenic determinant.

8. The method of claim 1, wherein the heterologous RNA encodes a protein or a polypeptide having therapeutic activity.

9. The method of claim 1, in which the alphavirus base sequence having translation enhancing activity provides at least a 4-fold increase in translation activity.

10. The method of claim 1, in which the alphavirus base sequence having translation enhancing activity provides at least a 6-fold increase in translation activity.

11. The method of claim 1, in which the alphavirus base sequence having translation enhancing activity provides at least an 8-fold increase in translation activity.

12. The method of claim 3, wherein the translation enhancing base sequence comprises the nucleotide sequence of SEQ ID NO:1.

13. A method for producing a recombinant alphavirus comprising a recombinant alphavirus RNA genome surrounded by a wild-type alphavirus coat;
the RNA genome comprising a self-replicative and transcription competent recombinant alphavirus RNA molecule comprising at least part of an alphavirus RNA genome and heterologous RNA encoding a substance having biological activity located downstream of and operatively linked to an alphavirus base sequence having translation enhancing activity, the translation enhancing base sequence being comprised of a complete alphavirus capsid gene or a portion thereof;
comprising:
i) introducing a DNA molecule, which comprises DNA sequences complementary to the recombinant RNA genome operatively linked to a promoter functional in a cell, and a DNA molecule comprising DNA sequences complementary to a helper RNA encoding alphavirus structural proteins and comprising coding sequences for the alphavirus structural proteins, cis acting replication signals but no encapsidation signals into said cell;
ii) producing infectious recombinant alphavirus particles by incubating the cells in a medium; and
iii) collecting the medium containing infectious recombinant alphavirus particles.

14. The method of claim 13, wherein the promoter is a SP6 promoter.

15. The method of claim 13, in which the alphavirus base sequence having translation enhancing activity provides at least a 4-fold increase in translation activity.

16. The method of claim 13, in which the alphavirus base sequence having translation enhancing activity provides at least a 6-fold increase in translation activity.

17. The method of claim 13, in which the alphavirus base sequence having translation enhancing activity provides at least an 8-fold increase in translation activity.

18. A cultured transformed cell comprising:
i) a recombinant alphavirus RNA genome; the RNA genome comprising a self-replicative and transcription competent recombinant alphavirus RNA molecule comprising at least part of an alphavirus RNA genome and heterologous RNA encoding a substance having biological activity located downstream of and operatively linked to an alphavirus base sequence having translation enhancing activity, the translation enhancing base sequence being comprised of a complete alphavirus capsid gene or a portion thereof; and
ii) a helper RNA encoding alphavirus structural proteins and comprising coding sequences for the alphavirus structural proteins, cis acting replication signals but no encapsidation signals, which cell can produce infectious recombinant alphavirus particles comprising the said recombinant RNA surrounded by a wild type alphavirus coat.

19. The transformed cell of claim 18, in which the heterologous gene product is expressed in the cells as a fusion product with the complete capsid protein or with an amino terminal portion of the capsid protein encoded by a portion of the capsid gene.

20. The transformed cell of claim 18, wherein the alphavirus is Semliki Forest virus.

21. The transformed cell of claim 18, wherein the translation enhancing base sequence comprises residues 1 to 102 of SEQ ID NO:1.

22. The transformed cell of claim 18, wherein the translation enhancing base sequence comprises residues 1 to 81 of SEQ ID NO:1.

23. The transformed cell of claim 18, wherein the translation enhancing base sequence comprises the nucleotide sequence of SEQ ID NO:1.

24. The transformed cell of claim 18, wherein the heterologous RNA is expressed as a fusion product that is cleaved at its fusion site by the autolytic protease activity of the capsid protein.

25. The transformed cell of claim 18, wherein the heterologous RNA sequence encodes a protein or a polypeptide comprising an antigenic determinant.

26. The transformed cell of claim 18, wherein the heterologous RNA encodes a protein or a polypeptide having therapeutic activity.

27. The transformed cell of claim 18, in which the alphavirus base sequence having translation enhancing activity provides at least a 4-fold increase in translation activity.

28. The transformed cell of claim 18, in which the alphavirus base sequence having translation enhancing activity provides at least a 6-fold increase in translation activity.

29. The transformed cell of claim 18, in which the alphavirus base sequence having translation enhancing activity provides at least an 8-fold increase in translation activity.

30. An infectious recombinant alphavirus particle comprising a recombinant alphavirus RNA genome surrounded by a wild-type alphavirus coat; the RNA genome comprising a self-replicative and transcription competent recombinant alphavirus RNA molecule comprising at least part of an alphavirus RNA genome and heterologous RNA encoding a substance having biological activity located downstream of and operatively linked to an alphavirus base sequence having translation enhancing activity, the translation enhancing base sequence being comprised of a complete alphavirus capsid gene or a portion thereof.

31. The infectious recombinant alphavirus particle of claim 30, in which the heterologous RNA is is fused with the complete capsid gene at its 3' end or is fused to the 3' end of an amino terminal portion of the capsid gene.

32. The infectious recombinant alphavirus particle of claim 30, wherein the alphavirus is Semliki Forest virus.

33. The infectious recombinant alphavirus particle of claim 30, wherein the translation enhancing base sequence comprises residues 1 to 102 of SEQ ID NO:1.

34. The infectious recombinant alphavirus particle of claim 30, wherein the translation enhancing base sequence comprises the residues 1 to 81 of SEQ ID NO:1.

35. The infectious recombinant alphavirus particle of claim 30, wherein the translation enhancing base sequence comprises the nucleotide sequence of SEQ ID NO:1.

36. The infectious recombinant alphavirus particle of claim 30, wherein the heterologous RNA is expressed as a fusion product that is cleaved at its fusion site by the autolytic protease activity of the capsid protein.

37. The infectious recombinant alphavirus particle of claim 30, wherein the heterologous RNA sequence encodes a protein or a polypeptide comprising an antigenic determinant.

38. The infectious recombinant alphavirus particle of claim 30, wherein the heterologous RNA encodes a protein or a polypeptide having therapeutic activity.

39. The infectious recombinant alphavirus particle of claim 30, in which the alphavirus base sequence having translation enhancing activity provides at least a 4-fold increase in translation activity.

40. The infectious recombinant alphavirus particle of claim 30, in which the alphavirus base sequence having translation enhancing activity provides at least a 6-fold increase in translation activity.

41. The infectious recombinant alphavirus particle of claim 30, in which the alphavirus base sequence having translation enhancing activity provides at least a 4-fold increase in translation activity.

42. A method for producing a substance having biological activity comprising:

infecting a cell in culture with a recombinant alphavirus particle of claim 30, thereby expressing the heterologous RNA to obtain a substance having biological activity; and separating the substance having biological activity from the cell or from a culture medium; and optionally purifying the substance having biological activity.

43. A method for producing a substance having biological activity comprising:

infecting a cell in an animal with a recombinant alphavirus particle of claim 30, thereby expressing the heterologous RNA to obtain a substance having biological activity; and separating the substance having biological activity from a tissue or body fluid of the animal; and optionally purifying the substance having biological activity.

44. A vaccine composition comprising the recombinant alphavirus particle of claim 30, in which the heterologous RNA encodes an immunogenic protein, polypeptide or peptide, and a pharmaceutically acceptable carrier.

45. A transformed cell in culture comprising a recombinant alphavirus RNA genome surrounded by a wild-type alphavirus coat; the RNA genome comprising a self-replicative and transcription competent recombinant alphavirus RNA molecule comprising at least part of an alphavirus genome and a heterologous RNA encoding a substance having a biological activity, the heterologous RNA being located downstream from and operatively linked to an alphavirus nucleotide sequence having translation enhancing activity, the translation enhancing nucleotide sequence being comprised of a complete alphavirus capsid protein gene or a portion thereof.

46. The method of claim 42, wherein the substance having biological activity is a protein, a polypeptide or a peptide.

47. The method of claim 42, wherein the substance having biological activity is a protein, a polypeptide or a peptide.

48. The vaccine composition of claim 44, in which the alphavirus base sequence having translation enhancing activity provides at least a 4-fold increase in translation activity.

49. The vaccine composition of claim 44, in which the alphavirus base sequence having translation enhancing activity provides at least an 8-fold increase in translation activity.

50. A method for immunizing a subject comprising administering to said subject the vaccine composition of claim 44.

* * * * *